United States Patent
Ritz

(10) Patent No.: US 7,949,471 B2
(45) Date of Patent: May 24, 2011

(54) METHOD AND SYSTEM OF MEASURING CETANE VALUES FOR MIDDLE DISTILLATE FUELS

(75) Inventor: G. Patrick Ritz, Irvine, CA (US)

(73) Assignee: Petroleum Analyzer Company, LP, Houston, TX (US)

(*) Notice: Subject to any disclaimer, the term of this patent is extended or adjusted under 35 U.S.C. 154(b) by 647 days.

(21) Appl. No.: 11/949,600

(22) Filed: Dec. 3, 2007

(65) Prior Publication Data

US 2008/0257017 A1 Oct. 23, 2008

Related U.S. Application Data

(60) Provisional application No. 60/868,273, filed on Dec. 1, 2006.

(51) Int. Cl.
*G01N 30/16* (2006.01)
(52) U.S. Cl. ............... 702/11; 702/22; 702/24; 702/27
(58) Field of Classification Search ............ 702/11, 702/22, 24, 25, 98, 100, 130, 140, 176, 179, 702/182, 183; 73/35.02; 95/149; 436/164; 701/114
See application file for complete search history.

(56) References Cited

U.S. PATENT DOCUMENTS

| | | | | |
|---|---|---|---|---|
| 5,457,985 A * | 10/1995 | Cellier et al. | ........... | 73/35.02 |
| 6,096,560 A * | 8/2000 | Scripca et al. | ........... | 436/164 |
| 6,284,022 B1 * | 9/2001 | Sachweh et al. | ........... | 95/149 |
| 6,609,413 B1 * | 8/2003 | De Craecker | ........... | 73/35.02 |
| 7,487,663 B2 * | 2/2009 | Sobotowski et al. | ........ | 73/35.02 |
| 7,529,616 B2 * | 5/2009 | Bizub | ........... | 701/114 |
| 2005/0256352 A1 * | 11/2005 | Clark et al. | ........... | 585/14 |
| 2007/0079647 A1 * | 4/2007 | Aoyama | ........... | 73/35.02 |
| 2007/0246005 A1 | 10/2007 | Sobotowski | | |

FOREIGN PATENT DOCUMENTS

DE WO 2006/136349 12/2006
EP 0 737 862 A 10/1996

OTHER PUBLICATIONS

Determination of Ignition Delay and Derived CETANE Number (DCN) of Diesel Oils by Combustion in a Constant Volume Chamber, ASTM Designation, ASTM International, US, vol. D6890-4, May 2004.
Hashimoto et al. "Evaluation of ignition quality of lpg with cetane number improver," SAE Technical Paper Series 2002-01-0870, 2002, XP002473484.
PCT ISR and Written Opinion to PCT Counterpart.
PCT ISR and Written Opinion of related PCT counterpart.
U.S. Appl. No. 11/949,610, filed Dec. 3, 2007—related case.
R.D. Matthews, Mechanical Engineer's Handbook: Energy and Power, vol. 4, 3rd ed., Chpt. 27, Feb. 16, 2006, John Wiley & Sons, Inc. XP002473653.
Ryan III & Matheaus, "Fuel requirements for HCCI engine operation," SAE Paper 2003-01-1813, 2003, XP002473652.

* cited by examiner

*Primary Examiner* — Mohamed Charioui
*Assistant Examiner* — Felix E Suarez
(74) *Attorney, Agent, or Firm* — Gunn Lee & Cave, P.C.

(57) ABSTRACT

A method and a system is disclosed for determining cetane values from constant volume combustion chamber apparatuses capable of producing pressure versus time combustion profiles having a fast combustion region and a slow combustion region, where data from the two regions is used to compute cetane values for middle distillate fluid samples using a series expansion equation.

41 Claims, 10 Drawing Sheets

Combustion Pressure Curves Showing Two Combustion Regions

METHOD AND SYSTEM OF MEASURING CETANE VALUES FOR MIDDLE DISTILLATE FUELS

RELATED APPLICATIONS

The present application claims priority to U.S. Provisional Patent Application Ser. No. 60/868,273 filed 1 Dec. 2006.

BACKGROUND OF THE INVENTION

1. Field of the Invention

The present invention relates to a method and a system for calculating or measuring cetane number values of middle distillate fluids and/or fuels.

More particularly, the present invention relates to a method and a system for measuring cetane number values of middle distillate fluids and/or fuels, where the method includes combusting a sample of a middle distillate fluid and/or fuel in a constant volume combustion chamber (CVCC) under conditions to produce combustion data of pressure versus time or a combustion pressure versus time profile and deriving or calculating a cetane number value from data points selected from the pressure versus time profile or from data points and data point ratios or from data point ratio.

2. Description of the Related Art

Current methods and systems for measuring cetane value are based either on engine data or are based on data derived from a constant volume combustion chamber. The methods and systems utilizing constant volume combustion chamber apparatuses determine a cetane value from an equation that uses a single point from pressure versus time combustion data that corresponds to a given increase in chamber pressure after injection of a fuel sample. These methods are wrought with uncertainty for fuels having different amounts of faster burning fuel components and using apparatuses that are capable of differentiating between faster and slower burning fuel components.

Thus, there is a need in the art for methods and systems for determining cetane values from constant volume combustion chamber apparatuses, especially in apparatuses capable of differentiating between faster and slower burning fluid components, where the methods and systems utilize data a pressure versus time profile in a series expansion about selected data points or selected points and ratios of the selected points or ratio of the selected points from the curve to derive improved cetane number values for middle distillate fluids and/or fuels.

SUMMARY OF THE INVENTION

The present invention provides a system and method capable of determining cetane number values from a pressure versus time combustion profile of a middle distillate, where the data or profile includes a single combustion region or multiple combustion regions.

The present invention also provides a system and method capable of determining cetane number values from a pressure versus time combustion profile of a middle distillate, where the data or profile includes a first region, an A region or early ignition delay region, and a second region, a B region or late ignition delay region. The A region represents fluid/fuel components having a first combustion rate and the B region represents fluid/fuel components having a second combustion rate, where the first combustion rate is faster than the second combustion rate.

The present invention provides a system for computing cetane number values of middle distillate fluids and/or fuels including a constant volume combustion chamber (CVCC) subsystem having a pressure sensor, a source of an oxidizing agent, a middle distillate fluid/fuel source, a pressurizing means and a heating means. The system also includes an analyzing subsystem adapted to accumulate data during combustion of a sample in the CVCC subsystem to produce a pressure versus time data profile, and to compute a derived cetane number value from at least one data point selected from the data profile as an independent variable in a power series expansion about the selected data points or about the selected data points and ratios of the selected data points or about ratio of the selected data points.

The present invention provides a system for computing cetane number values of middle distillate fluids and/or fuels including a constant volume combustion chamber (CVCC) subsystem having a pressure sensor, a source of an oxidizing agent, a middle distillate fluid/fuel source, a pressurizing means and a heating means. For combustion data profiles that include two combustion regions, an A region and a B region, the system also includes an analyzing subsystem adapted to accumulate data during combustion of a sample in the CVCC subsystem to produce pressure versus time data profile, and to compute a derived cetane number value from at least one point selected from either the A region or the B region as an independent variable in a power series expansion about the selected data points or about the selected data points and ratios of the selected data points or about ratios of the selected data points. In certain embodiments, the ratios are between selected data points from region A to selected data points from region B, i.e., $ID_A/ID_B$, where $ID_A$ is a selected data point from region A and $ID_B$ is a selected data point from region B.

The present invention provides a system for computing cetane number values of middle distillate fluids and/or fuels including a constant volume combustion chamber (CVCC) subsystem having a pressure sensor, a source of an oxidizing agent, a middle distillate fluid/fuel source, a pressurizing means and a heating means. For combustion data profiles that include two combustion regions, an A region and a B region, the system also includes an analyzing subsystem adapted to accumulate data during combustion of a sample in the CVCC subsystem to produce pressure versus time data profile, and to compute a derived cetane number value from at least one point selected from at least one data point selected from the A region and at least one data point selected from the B region as independent variables in a power series expansion about the selected points or about the selected data points and ratios of the selected data points from region A to the selected data points from region B or about ratios of the selected data points from region A to the selected data points from region B.

The present invention also provides a method including the step of combusting a sample of a middle distillate fluid and/or fuel in a constant volume combustion chamber (CVCC) apparatus having a pressure sensor to produce combustion pressure versus time data, plottable as a pressure versus time profile. The method also includes the step of selecting at least one data point from the profile as an independent variable for a power series expansion about the selected point or points. The method also includes the step of computing a derived cetane number value utilizing the selected point or points as independent variables in a power series expansion about the selected points, where the derived cetane number value has a greater accuracy than a cetane number value calculated from a non-power series expansion using only a specific point from the same data. The method can also include the step of calibrating coefficients of the expansion equation using sample with known cetane number values.

The present invention also provides a method including the step of combusting a sample of a middle distillate fluid and/or fuel in a constant volume combustion chamber (CVCC) apparatus having a pressure sensor to produce combustion pressure versus time data, plottable as a pressure versus time profile. For data profiles that include a first region, the A region, and a second region, the B region, the method also includes the step of selecting at least one data point from the profile as the independent variable for a power series expansion about the selected point or points. The selected points can include one or more points from either the first region of the profile corresponding to ignition of faster burning components of the fluid/fuel or the second region of the profile corresponding to ignition of slower burning components of the fluid/fuel or both. The method also includes the step of computing a derived cetane number value utilizing the selected point or points as independent variables in a power series expansion about the selected points, where the derived cetane number value has a greater accuracy than a cetane number value calculated from a non-power series expansion using only a specific point from the same data. The method can also include the step of calibrating coefficients of the expansion equation using sample with known cetane number values.

The present invention also provides a method including the step of combusting a sample of a middle distillate fluid and/or fuel in a constant volume combustion chamber (CVCC) apparatus having a pressure sensor to produce combustion pressure versus time data, plotted as a pressure versus time profile. For data profiles that include a first region, the A region, and a second region, the B region, the method also includes the step of selecting at least one point from the A region and at least one point from the B region. The method also includes the step of deriving a cetane number value from an equation using the at least one point from the A region and the at least one point from the B region as independent variables in a power series expansion about the point to compute a derived cetane number value that is closer to an actual cetane number value of the sample as compared to computing a cetane number value from a non-power series expansion using only a specific point from the same data. The method can also include the step of calibrating coefficients of the expansion equation using sample with known cetane number values.

The present invention also provides a method for determining coefficients of a series expansion equation for calculating derived cetane number values comprising the step of combusting a sample having a known cetane number value in a constant volume combustion chamber apparatus under controlled conditions to obtain pressure versus time combustion data. Next, at least one point from the profile is selected and a derived cetane number value using the series expansion equation about the selected points with a set of initial coefficients is computed or calculated. Next, the coefficients of the series expansion equation are adjusted so that a difference between the cetane number and the derived cetane number value is minimized.

BRIEF DESCRIPTION OF THE DRAWINGS

The invention can be better understood with reference to the following detailed description together with the appended illustrative drawings in which like elements are numbered the same.

DETAILED DESCRIPTION OF THE INVENTION

Figure 1:
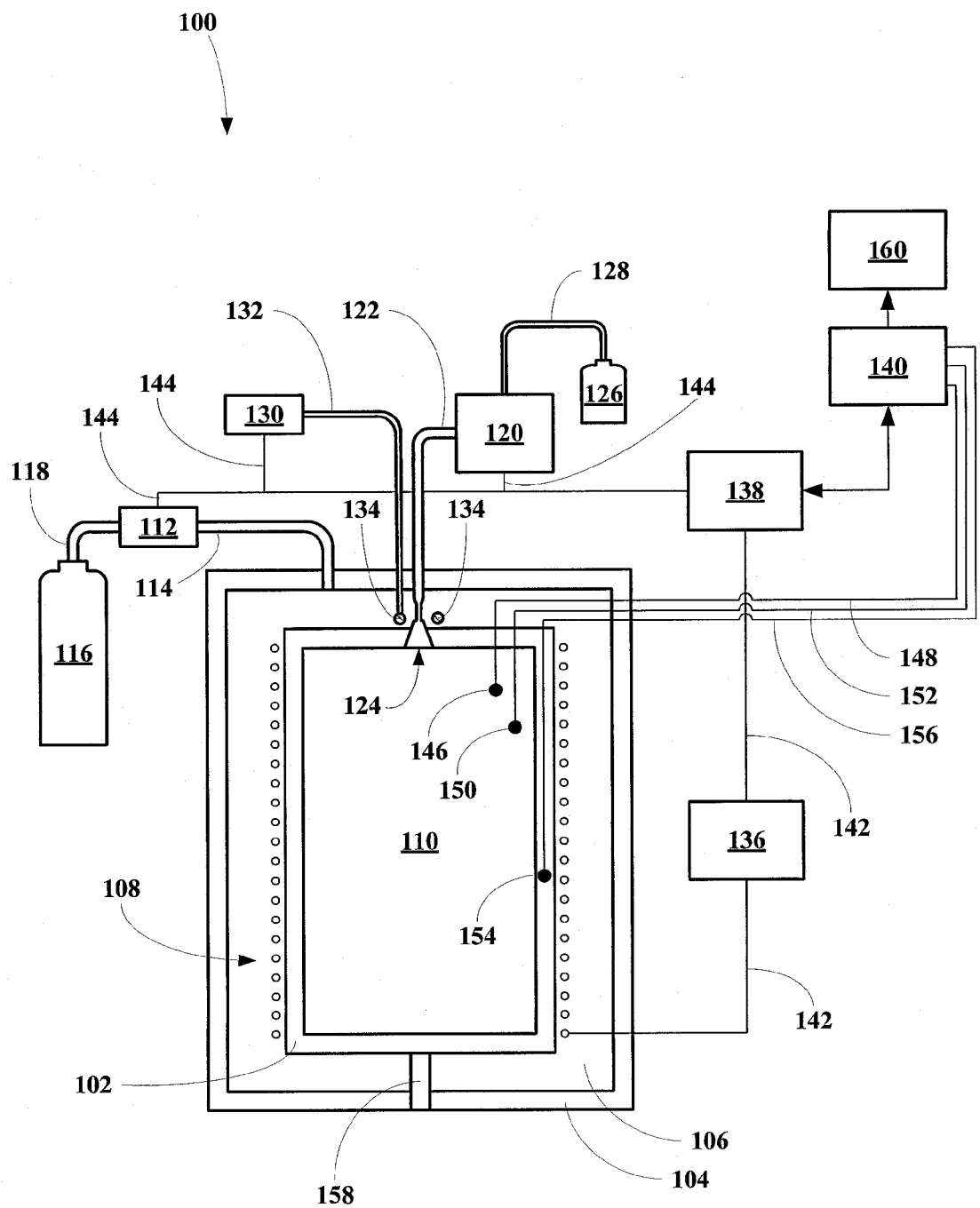
FIG. 1 depicts a constant volume combustion chamber (CVCC) apparatus for measuring time/pressure profiles of samples to be combusted.

The inventor has found that a new method can be formulated for determining derived cetane number values of middle distillates from combustion data derived from a constant volume combustion chamber (CVCC) apparatus. The inventor has found that superior derived cetane number values can be calculated using a series expansion equation, expanded about one data point or a plurality of data points from pressure versus time data collected when a middle distillate fluid and/or fuel sample is burned in the CVCC apparatus. The inventor has found that superior cetane number values can be obtained using the CVCC capable of yielding a pressure/time profile including multiple combustion regions. For example, certain pressure/time profiles include an A region and a B region, where the A region represents fuel components with shorter (early) ignition delay times (faster burning components) and the B region represents fuel components with longer (later) ignition delay times (slower burning components). The inventor has found cetane number calculations using at least one data point selected from each combustion region as the independent variables yield superior derived cetane number values than calculations based on only a single, specific pressure/time data point. For example, in profiles having an A region and a B region, cetane number values derived from equations using at least one point from the A region and at least one data point selected from the B region yield superior derived cetane number values than calculations based on only a single, specific pressure/time data point.

The present invention broadly relates to a system for determining or calculating cetane number values for known and/or unknown middle distillate fluid and/or fuel samples. The system includes a combustion subsystem comprising a constant volume combustion chamber (CVCC) apparatus for obtaining pressure versus time data from the combustion of a known or unknown middle distillate fluid and/or fuel sample. The system also includes an analyzing subsystem for selecting at least one data point as an independent variable in an expansion equation capable of calculating a derived cetane number value from the at least one selected point as the independent variable in the equation. For data that has multiple regions, at least one data point is selected from each region as independent variables in calculating a derived cetane number value. The calculation can also include ratios of data points from each region. In certain embodiments, the ratios are between data points from the regions corresponding to earlier ignition components and later ignition components. In other embodiments, the calculation uses just the ratios of the selected data points. For data that has A and B regions, at least one point is selected from the A region and at least one point is selected from the B region as independent variables in calculating a derived cetane number value. In certain embodiments, the calculation also utilizes ratios of selected data points as additional independent variables. In other embodiments, the calculation uses just ratios of selected points. In other embodiments, the ratios are selected data points from region A to selected data points from region B, i.e., $ID_A/ID_B$, where $ID_A$ is a selected data point from region A and $ID_B$ is a selected data point from region B.

The present invention also broadly relates to a method including the step of combusting a sample of a middle distillate fluid and/or fuel in a constant volume combustion chamber (CVCC) apparatus having a pressure sensor and/or a temperature sensor to produce combustion pressure versus time data, plotted as a pressure versus time profile. The method also includes the step of selecting at least one data point. The method also includes the step of calculating or computing a derived cetane number value utilizing the at least one data point as an independent variable in an expansion equation. For profiles that include multiple regions, the selecting step includes selecting at least one point from each region. For profiles that include A and B regions, the selecting step includes selecting at least one data point from the A region and at least one data point from the B region as independent variables, where the A region corresponds to the ignition of faster burning components of the fluid/fuel and the B region corresponds to the ignition of slower burning components of the fluid/fuel. The method also includes the step of computing a derived cetane number value utilizing the selected data points, utilizing the selected data points and ratios of the selected data points, or utilizing ratios of the selected data points from the regions as independent variables in an expansion equation. The method can also include the step of calibrating coefficients of the expansion equation using sample with known cetane number values.

Suitable Reagents

Suitable middle distillate fluids and/or fuels includes, without limitation, any hydrocarbon fluid or fuel that has a middle boiling point in the context of refined hydrocarbons derived from crude oil or bio-material fluids or fuels or synthetic fluids or fuels with boiling points in the range of middle boiling point refined hydrocarbons, or mixtures or combinations thereof. Non-limiting exemplary examples of such fluids include diesel fuels, diesel fuels with cetane improving additives, jet fuels, bio-diesel fuels, kerosenes, or the like. Although generally middle distillates are hydrocarbons that include primarily gas oil and aviation jet fuel (or high-grade kerosene), the inventors use it here to refer not only to the distillates derived from the processing of crude oil, but also fuels derived from bio-materials, so called bio-diesels, and fuels derived from Fischer-Tropsch catalytic polymerization of hydrogen/carbon monoxide mixture, so called syn-gas, into hydrocarbon fuels with in the middle distillate range. Gas oil is increasingly used as an industrial fuel, displacing fuel oil because of environmental concerns. It is also used as a fuel for buses, lorries, and taxis. Jet fuel is commonly used as an aviation fuel and also as a domestic fuel for heating purposes.

Specific Embodiments of the System and Method

The system and method of this invention utilize data derived from a constant volume combustion chamber (CVCC) apparatus to compute a derived cetane number value for a middle distillate fluid/fuel, where a middle distillate fluid/fuel sample is combusted at an elevated temperature and pressure. The sample is injected into the CVCC apparatus at a predetermined pressure and temperature. After injection, a pressure in the chamber is measured as a function of time after injection until combustion is complete.

In prior art methods, a single data point from the pressure/time data representing an ignition delay was selected to be used in an equation to compute or calculate a derived cetane number (DCN) that would correspond to a cetane number (CN) measured using a special internal combustion engine. However, with the advent of new fuel mixtures, such as fuels containing additives such as cetane improvers, the derived cetane number values have shown mark deviations from the actual cetane number values.

Using newer CVCC apparatuses to combust samples, pressure/time profiles are produced that show a single region or multiple regions. In certain samples, the pressure/time profile has only a single region. In other samples, the profile shows a main region having a shoulder. In other samples, the profile has two distinct regions. The first region or shoulder evidences early burning components, while the main profile or second region evidence late burning components. The first region, sometimes referred to herein as the A region, represents fluid/fuel components that have a shorter ignition delay (start burning earlier), and the second region, sometimes referred to herein as the B region, represents fluid/fuel components that have a longer ignition delay (start burning later).

Because fluids/fuels generally give rise to a two region pressure/time profile when tested in newer CVCCs, the DCN values show considerable and inconsistent disagreement with their corresponding actual CN values. The present method significantly reduces these variances, by using at least one data point from each region, at least one data point from each region and ratios of the data points from different regions or ratios of data points from different regions of the pressure/time profile in a series expansion equation to generate DCN values having smaller variances from their corresponding actual CN values, where the expansion is relative to the selected data points, the selected points and ratios, or ratios as independent variables in the equation.

Detailed Description of a Constant Volume Combustion Chamber (Cvcc) Apparatus

Referring now to FIG. 1, a constant volume combustion chamber (CVCC) apparatus 100 for measuring pressure versus time data or data profiles of fluid samples for use in the methods of this invention, is shown. Using this type of CVCC apparatus, samples can be combusted in a controlled manner to yield pressure/time data generally having at least two combustion regions. From this data, at least one point from each region, e.g., an A region and a B region, can be selected and used as independent variables in a series expansion equation with respect to the selected values to derive improved DCN values for a fluid/fuel sample.

The apparatus 100 includes a combustion chamber 102 having a fixed capacity or volume. The combustion chamber 102 is surrounded by an outside container 104 adapted to accommodate a whole of the combustion chamber 102 in a sealed condition. Between the outer container 104 and the combustion chamber 102 is a thermal insulator 106 encasing a heater 108 adapted to heat an interior 110 of the combustion chamber 102 to a predetermined temperature. The apparatus 100 also includes a pressure regulator 112 for pressurizing the interior 110 of the combustion chamber 102 to a predetermined pressure via a compressed air feed conduit 114. The pressure regulator 112 is connected to a source of compressed air 116, which is used to adjust the pressure in the interior 110 to the predetermined pressure, via a compressed air supply conduit 118. The apparatus 100 also includes a high pressure injection system having an injector 120 for injecting a fuel sample into the combustion chamber 102 via a sample feed tube 122 through a nozzle 124. The sample is supplied to the injector 120 from a sample container 126 via a sample supply conduit 128 under pressure sufficient to inject the fuel sample into the combustion chamber 102. The apparatus 100 can optionally include a coolant pump 130 containing a coolant and adapted to circulate a coolant via a conduit 132 and ports 134 in the insulator 106 to cool the nozzle 124. The apparatus 100 also includes a power supply 136, a controller 138 and an analyzer 140, where the power supply 136 supplies power to the heater 108 and the controller 138 via power cables 142. The controller 138 is connect to the injector 120, the pressure regulator 112 and the coolant pump 130 via control cables 144 and is adapted to supply power to and control these devices so that a sample can be combusted in the combustion chamber 102 under controlled conditions. The analyzer 140 includes a pressure sensor 146 located in the interior 110 or on an interior surface of the chamber 102 and connected to the analyzer 140 by sensor cable 148. The analyzer 140 is adapted to receive pressure data from the pressure sensor 146 so that a time versus pressure profile can be recorded for each sample injected into the combustion chamber 102. The analyzer 140 also includes a first temperature sensor 150 located in the interior 110 of the combustion chamber 102 and connected to the analyzer 140 by a first temperature sensor cable 152, and a second temperature sensor 154 located in the wall of the combustion chamber 102 and connected to the analyzer 140 by a second temperature sensor cable 156. The analyzer 140 is adapted to receive temperature data from the sensors 150 and 154 so that a temperature of the combustion in the combustion chamber 102 can be controlled. The apparatus 100 also includes an exhaust port 158. The apparatus 100 can also includes an output device 160 such as a display device, a graphing device, a printer or a combination of these types of devices for outputting the raw data or cetane number values derived from the data in accordance with the method of this invention.

Once a sample has been combusted in an apparatus of FIG. 1 and its pressure/time data profile obtained, one data point or a plurality of data points from the profile are selected. The method can also include the step of calculating ratios between the selected points. The data point, data points and/or ratios are then used as an independent variable(s) in an equation comprising a power series expansion around the selected points to compute derived cetane number values having smaller variances with respect to their corresponding actual cetane number values. In certain embodiments, the data points include at least one data point from each combustion region discernible in the profile. In other embodiments, the data points include at least one point from the A region (early burning components) and at least one data point from the B region (later burning components). In other embodiments, the independent variables are data point ratios between data points from the earlier ignition regions to the later ignition regions, e.g., ratios of points from region A to points from region B. The coefficients in the series expansion are determined by fitting the equation to samples with known actual cetane number values, i.e., the equation is calibrated or tuned using standard or reference fluids/fuels having known cetane number values.

In one embodiment, a derived cetane number is calculated from second order equation (I):

$$DCN = C_{1a}ID_1 + C_{2a}ID_2 + C_{1b}(ID_1)^2 + C_{2b}(ID_2)^2 + I \quad (I)$$

where $ID_1$ is a data point selected from the A region of the pressure/time profile representing an ignition delay of components in the A region, $ID_2$ is a data point selected from the B region of the pressure/time profile representing an ignition delay of components in the B region, $C_{1a}$, $C_{1b}$, $C_{2a}$, and $C_{2b}$ are coefficients and I is the intercept, where the coefficients are obtained from solving equation (I) for a set of standard or reference samples with known cetane number values. In equation (I), the coefficients of $ID_1$ or $ID_2$ can be set to zero so that the derived cetane number values are calculated based on a power series expansion about a single ID measurement. It should be recognized that the value of the coefficients will change depending on the points selected.

In one embodiment, a derived cetane number is calculated from second order equation (II)

$$DCN = C_{1a}ID_1 + C_{2a}ID_2 + C_{1b}(ID_1)^2 + C_{2b}(ID_2)^2 + C_{ra}ID_1/ID_2 + C_{rb}(ID_1/ID_2)^2 + I \quad (II)$$

where $ID_1$ is a data point selected from the A region of the pressure/time profile representing an ignition delay of components in the A region, $ID_2$ is a data point selected from the B region of the pressure/time profile representing an ignition delay of components in the B region, $C_{1a}$, $C_{1b}$, $C_{2a}$, $C_{2b}$, $C_{ra}$, and $C_{rb}$ are coefficients and I is the intercept, where the coefficients are obtained from solving equation (II) for a set of standard or reference samples with known cetane number values. In equation (II), the coefficients of any of the terms can be set to zero so that the derived cetane number values are calculated based on a power series expansion about a single ID or a single ratio of selected data points. In a certain embodiment, the coefficient $C_{rb}$ is set equal to zero. It should be recognized that the value of the coefficients will change depending on the points selected.

In one embodiment, a derived cetane number is calculated from second order equation (III):

$$DCN = C_{ra}ID_1/ID_2 + C_{rb}(ID_1/ID_2)^2 + I \quad (III)$$

where $ID_1$ is a data point selected from the A region of the pressure/time profile representing an ignition delay of components in the A region, $ID_2$ is a data point selected from the B region of the pressure/time profile representing an ignition delay of components in the B region, $C_{ra}$ and $C_{rb}$ are coefficients and I is the intercept, where the coefficients are obtained from solving equation (III) for a set of standard or reference samples with known cetane number values. It should be recognized that the value of the coefficients will change depending on the points selected.

In another embodiment, the cetane number is calculated from a more generalized equation (IV):

$$DCN = \sum_{i=1, j=1}^{i=m, j=n} c_{ij} ID_i^j + \sum_{k=1, l=1}^{k=m, l=n} c_{kl} ID_k^l + I \quad (IV)$$

where $ID_i$ are data points selected from the A region of the profile representing an ignition delay of components in the A region, $ID_k$ are data points selected from the B region of the profile representing an ignition delay of components in the B region, $c_{ij}$ and $c_{kl}$ are coefficients and I is the intercept, i is an integer representing a number of data points selected from the A region, j is an integer representing the number of terms in the expansion for the selected data points in the A region, i.e., the power of the term, k is an integer representing the number of data points selected from the B region, and l is an integer representing the number of terms in the expansion for the selected data points in the B region, i.e., the power of the terms. The coefficients and intercept are obtained from solving equation (IV) for a set of standard or reference samples. The references or standard sample are a set of samples having well defined cetane number values (dependent variable), while the ID's (independent variables) are measured. The independent and dependent variables are substituted into the equation and the coefficients are determined using multiple linear regression. In equation (IV), the coefficients of $ID_i$ or $ID_k$ can be set to zero so that the derived cetane number values are calculated based on a power series expansion about either the $ID_i$ measurements or the $ID_k$ measurements.

In another embodiment, the cetane number is calculated from a more generalized equation (V):

$$DCN = \sum_{i=1, j=1}^{i=m, j=n} c_{ij} ID_i^j + \sum_{k=1, l=1}^{k=o, l=p} c_{kl} ID_k^l + \sum_{\substack{ii=1, jj=1, \\ kk=1}}^{\substack{ii=n, jj=o, \\ kk=m+p}} c_{iijjkk} \left(\frac{ID_{ii}}{ID_{jj}}\right)^{kk} + I \quad (V)$$

where $ID_i$ are data points selected from the A region of the profile representing an ignition delay of components in the A region, $ID_k$ are data points selected from the B region of the profile representing an ignition delay of components in the B region, and $ID_{ii}/ID_{jj}$ ratios of selected data points from the A region and $ID_{jj}$ are selected points from the B region, $c_{ij}$, $c_{kl}$ and $c_{iijjkk}$ are coefficients and I is the intercept, i is an integer representing a number of data points selected from the A region, j is an integer representing the number of terms in the expansion for the selected data points in the A region, i.e., the power of the term, k is an integer representing the number of data points selected from the B region, l is an integer representing the number of terms in the expansion for the selected data points in the B region, i.e., the power of the terms, ii is an integer representing the number of data points selected from the A region, jj is an integer representing the number of data points selected from the B region, kk is an integer representing the number of terms in the expansion for the ratios of selected data points from region A to selected data points from the B region, i.e., the power of the terms. The coefficients and intercept are obtained from solving equation (V) for a set of standard or reference samples. The references or standard sample are a set of samples having well defined cetane number values (dependent variable), while the ID's (independent variables) are measured. The independent and dependent variables are substituted into the equation and the coefficients are determined using multiple linear regression. In equation (V), any of the coefficients can be zero, provided at least one term from each summation has non zero coefficients.

In another embodiment, the cetane number is calculated from an even more generalized equation (VI):

$$DCN = \sum_{i=1}^{n} \sum_{j=1, k=1}^{j=m, k=o} c_{ijk} ID_j^k + I \quad (VI)$$

where $ID_j$ are data points selected from the $i^{th}$ region of the profile, where each region represents components having different ignition delay time and $c_{ijk}$ are expansion coefficients corresponding to the $i^{th}$ region, the $j^{th}$ point raised the kth power and I is the intercept. In Equation (VI), i is an integer representing a number of regions, j is an integer representing a number of data points selected from the $i^{th}$ region, k is an integer representing the number of terms in the expansion for the selected data points in expansion, i.e., the power of the term. The coefficients and intercept are obtained from solving equation (VI) for a set of standard or reference samples. The references or standard sample are a set of samples having well defined cetane number values (dependent variable), while the IDs (independent variables) are measured. The independent and dependent variables are substituted into the equation and the coefficients are determined using multiple linear regression. In equation (VI), the coefficients of all but one of the $ID_j$ can be set to zero so that the derived cetane number values are calculated based on a power series expansion about a single point in one region of the profile, a single point from two or all of the regions, a single point from one region and a plurality of points from the other regions, a single point from all regions save one and a plurality of points from the one region, or a plurality of points from each region.

In another embodiment, the cetane number is calculated from an even more generalized equation (VII):

$$DCN = \sum_{i=1}^{n} \sum_{j=1, k=1}^{j=m, k=o} c_{ijk} ID_j^k + \sum_{\substack{ii=1, jj=1, \\ kk=1}}^{\substack{ii=m, jj=m, \\ kk=o}} c_{iijjkk} \left(\frac{ID_{ii}}{ID_{jj}}\right)^{kk} + I \quad (VII)$$

where $ID_j$ are data points selected from the $i^{th}$ region of the profile, where each region represents components having different ignition delay time and $c_{ijk}$ are expansion coefficients corresponding to the $i^{th}$ region, the $j^{th}$ point of the $i^{th}$ region raised the $k^{th}$ power, $ID_{ii}/D_{jj}$ are ratios of data points from different regions, $c_{iijjkk}$ are expansion coefficients corresponding to the $ii^{th}$ data point from one region and the $jj^{th}$ data point from a different region raised to the $kk^{th}$ power and I is the intercept.

In the current ASTM standard method D 6890-03a for determining DCN values using a conventional CVCC system, the method includes a plot of the nozzle movement associated with the injection of a sample in milliseconds and a plot of the combustion profile of the injected sample with the time axis in milliseconds (ms) and the pressure axis in mega Pascals or Bar. The method then requires the selection of an ignition delay point where the pressure rises to a value of 0.02 MPa above the initial pressure. This point is then used in a standard equation to compute a derived cetane number (DCN). The data derived from these conventional CVCC systems generally show a combustion curve having only a single region, i.e., after ignition, the curve simply rises to a plateau.

Figure 2:
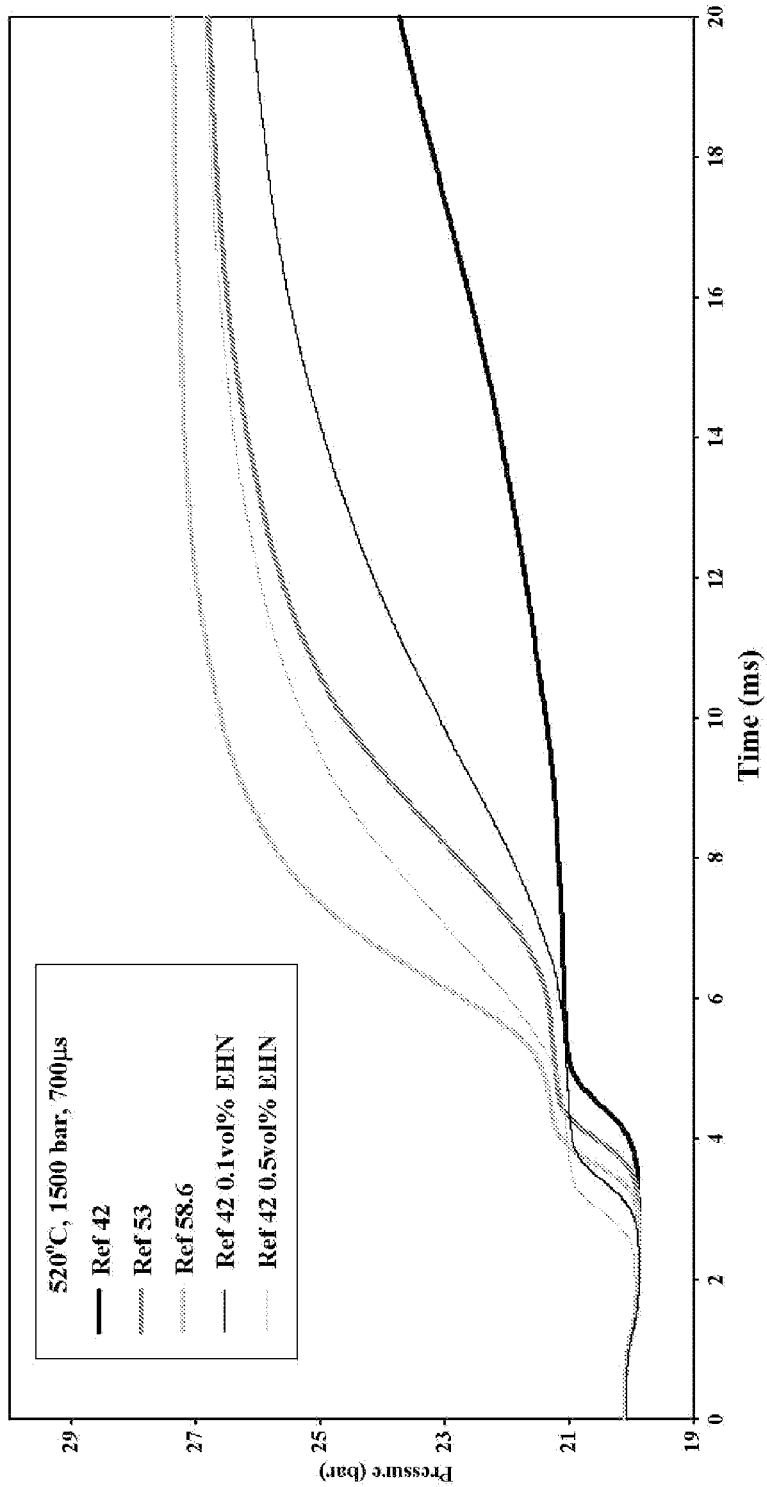
FIG. 2 depicts a plot of samples combusted using the apparatus of FIG. 1 showing two region profiles at 520° C., at 1500 bar, and t=700 μs.
Figure 3:
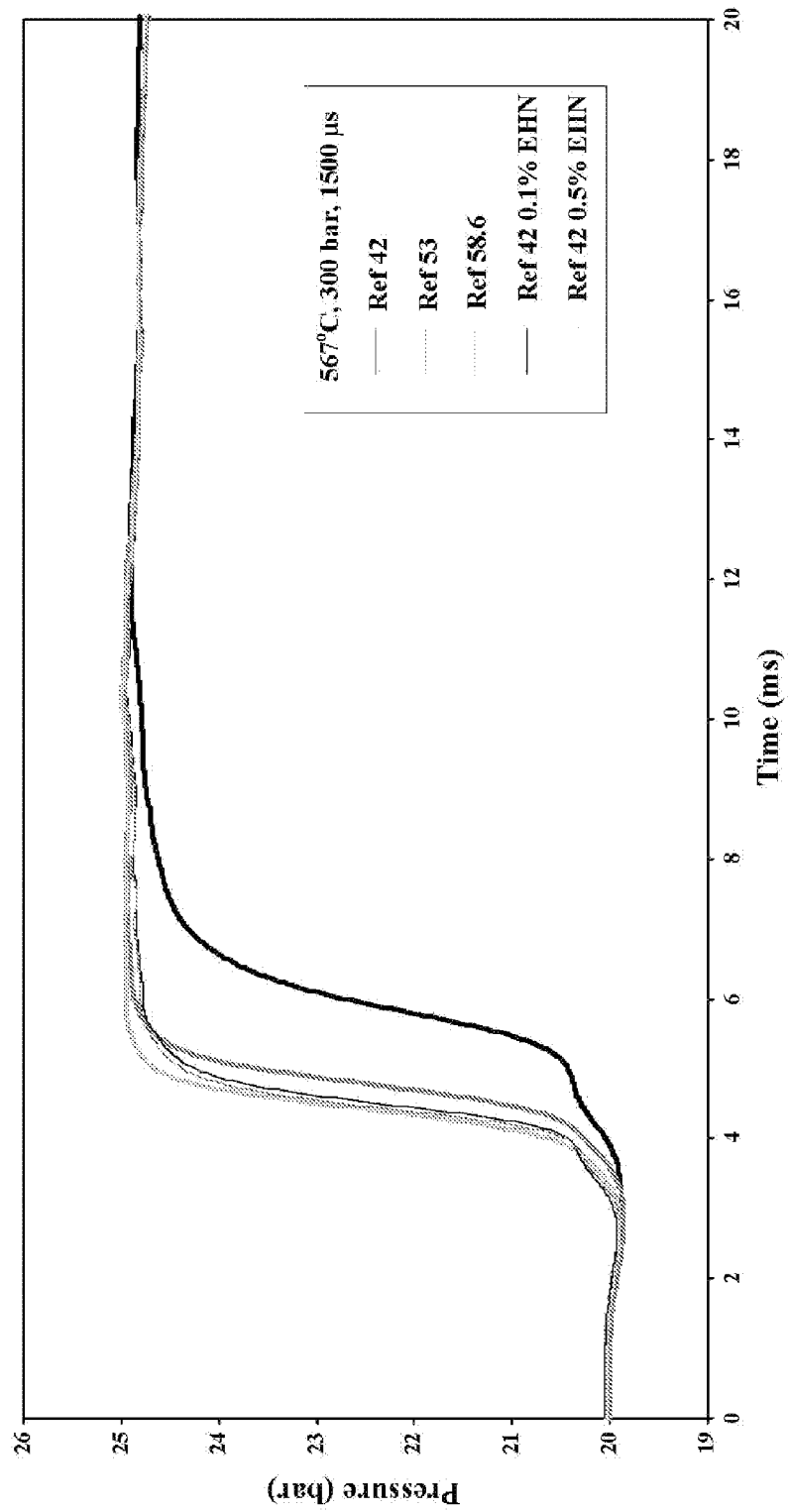
FIG. 3 depicts a plot of combustion samples using the apparatus of FIG. 1 showing two region profiles at 567° C., at 300 bar, and t=1500 μs.
Figure 4:
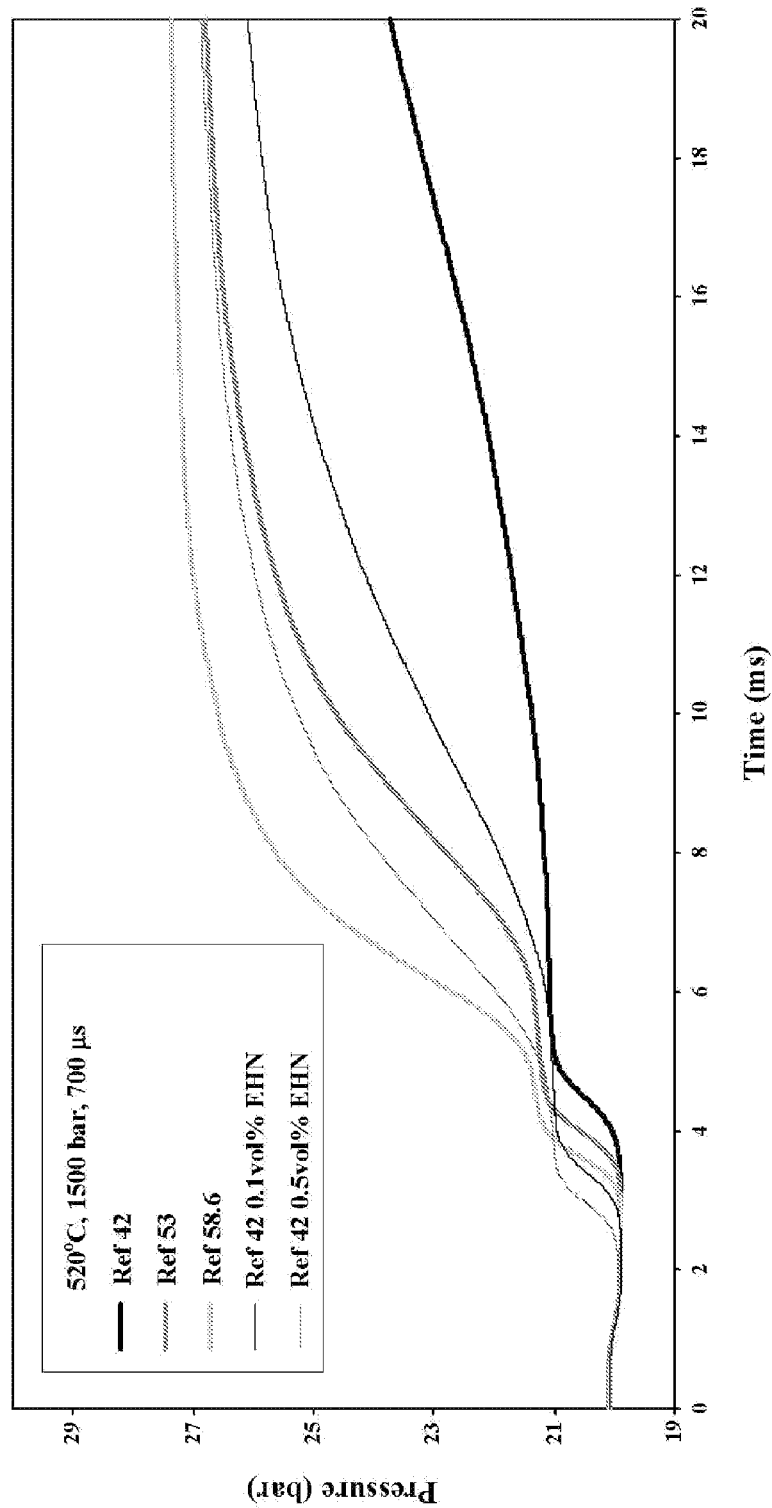
FIG. 4 depicts a plot of combustion samples using the apparatus of FIG. 1 showing two region profiles at 520° C., at 1500 bar, and t=700 μs.
Figure 5:
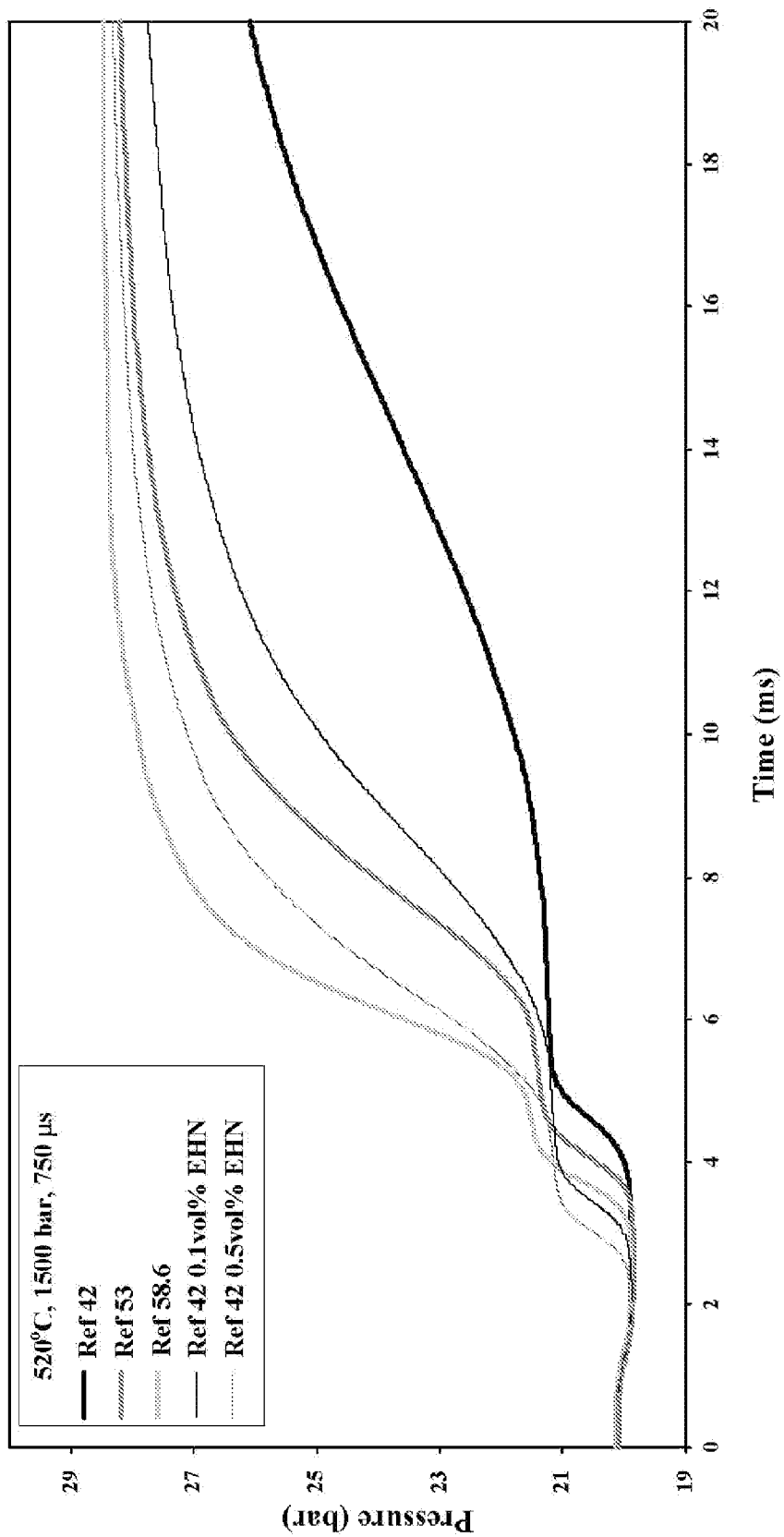
FIG. 5 depicts a plot of combustion samples using the apparatus of FIG. 1 showing two region profiles at 520° C., at 1500 bar, and t=750 μs.
Figure 6:
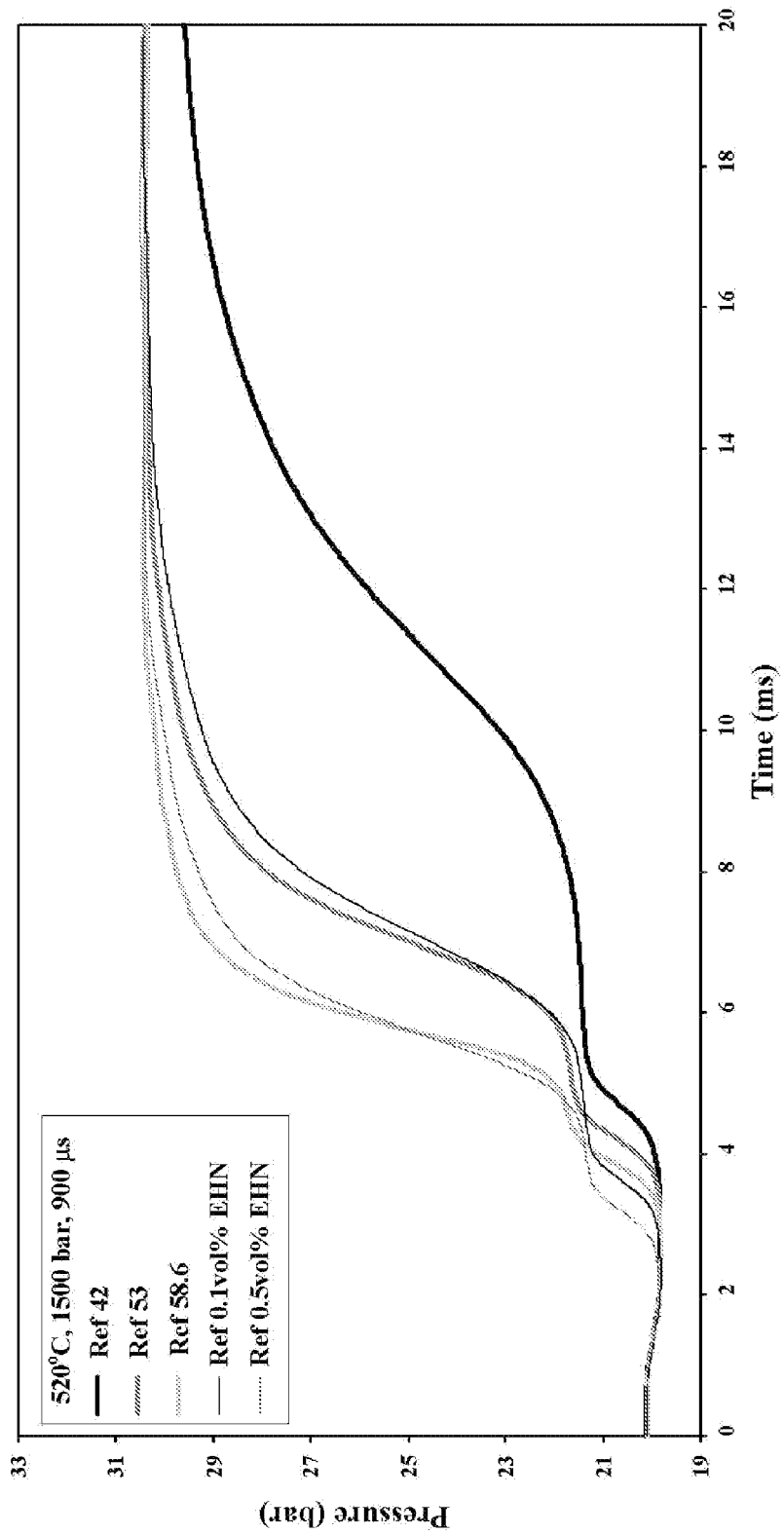
FIG. 6 depicts a plot of combustion samples using the apparatus of FIG. 1 showing two region profiles at 520° C., at 1500 bar, and t=900 μs.
Figure 7:
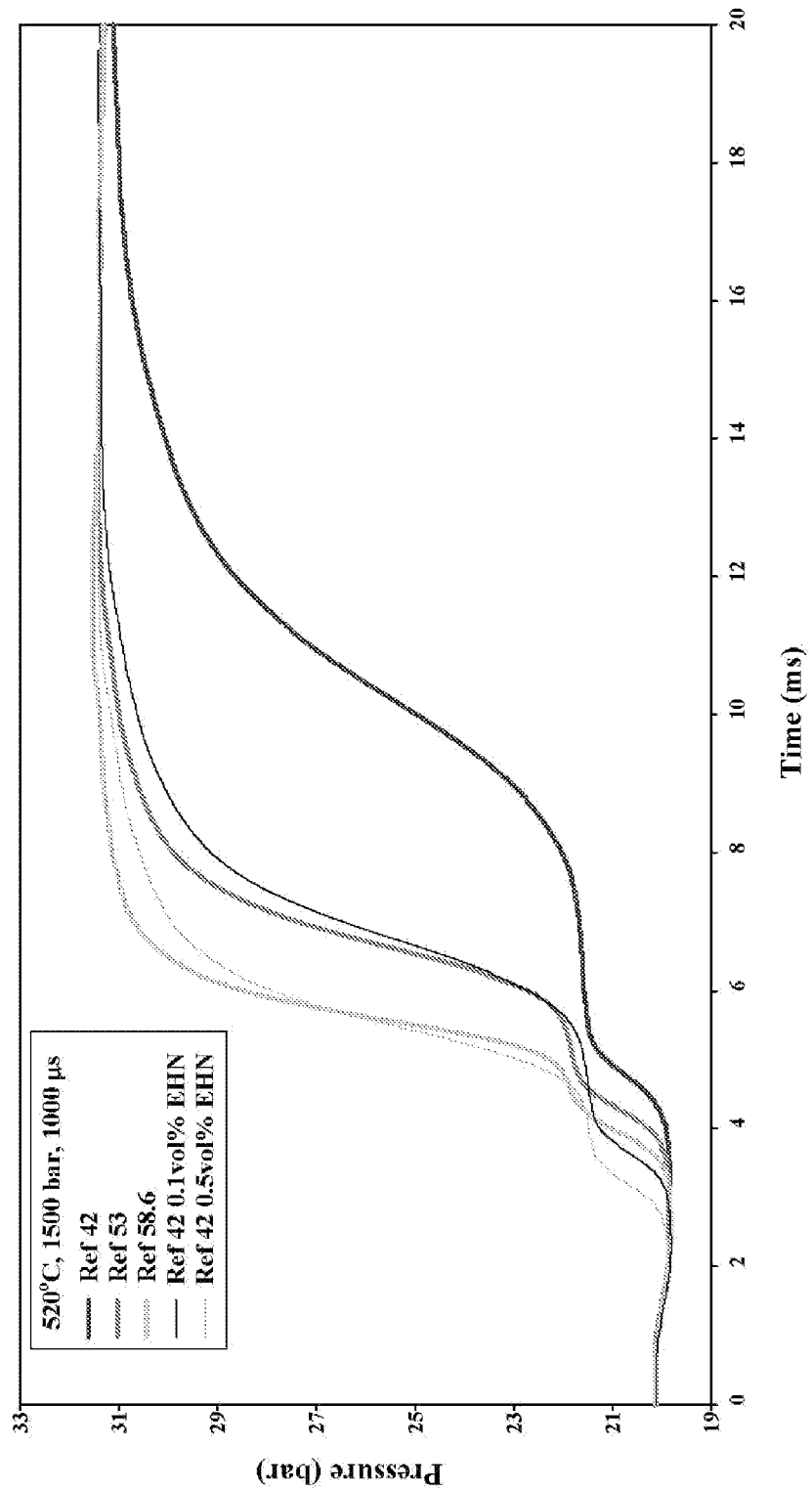
FIG. 7 depicts a plot of combustion samples using the apparatus of FIG. 1 showing two region profiles at 520° C., at 1500 bar, and t=1000 μs.
Figure 8:
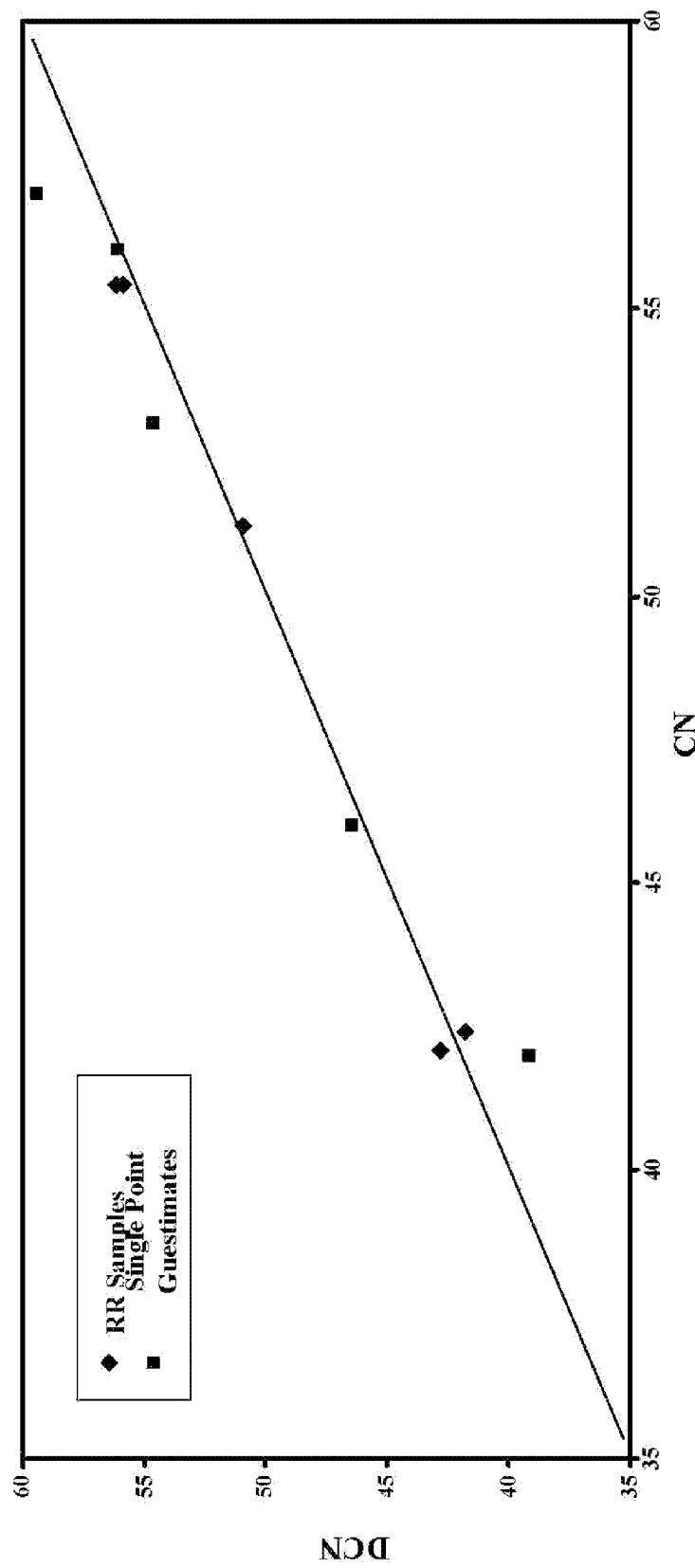
FIG. 8 depicts a plot of the correlations of derived cetane number values versus actual cetane number values.

Referring now to FIGS. 2&3, plots of combustion pressure/time profiles for two reference standards and three reference fluids/fuels are shown that were obtained using an apparatus of FIG. 1 at different temperatures, pressures and times. Referring now to FIGS. 4-7, plots of combustion pressure/time profiles for two reference standards and three reference fluids/fuels are shown that were obtained using an apparatus of FIG. 1 at different times at constant pressure and constant temperature. FIG. 8 displays a correlation of the DCN values and their corresponding CN values. It is clear that the data obtained using the apparatus of FIG. 1 yields pressure versus time profiles having two combustion regions, an early combustion region, the A region, and a late combustion region, the B region.

Figure 9:
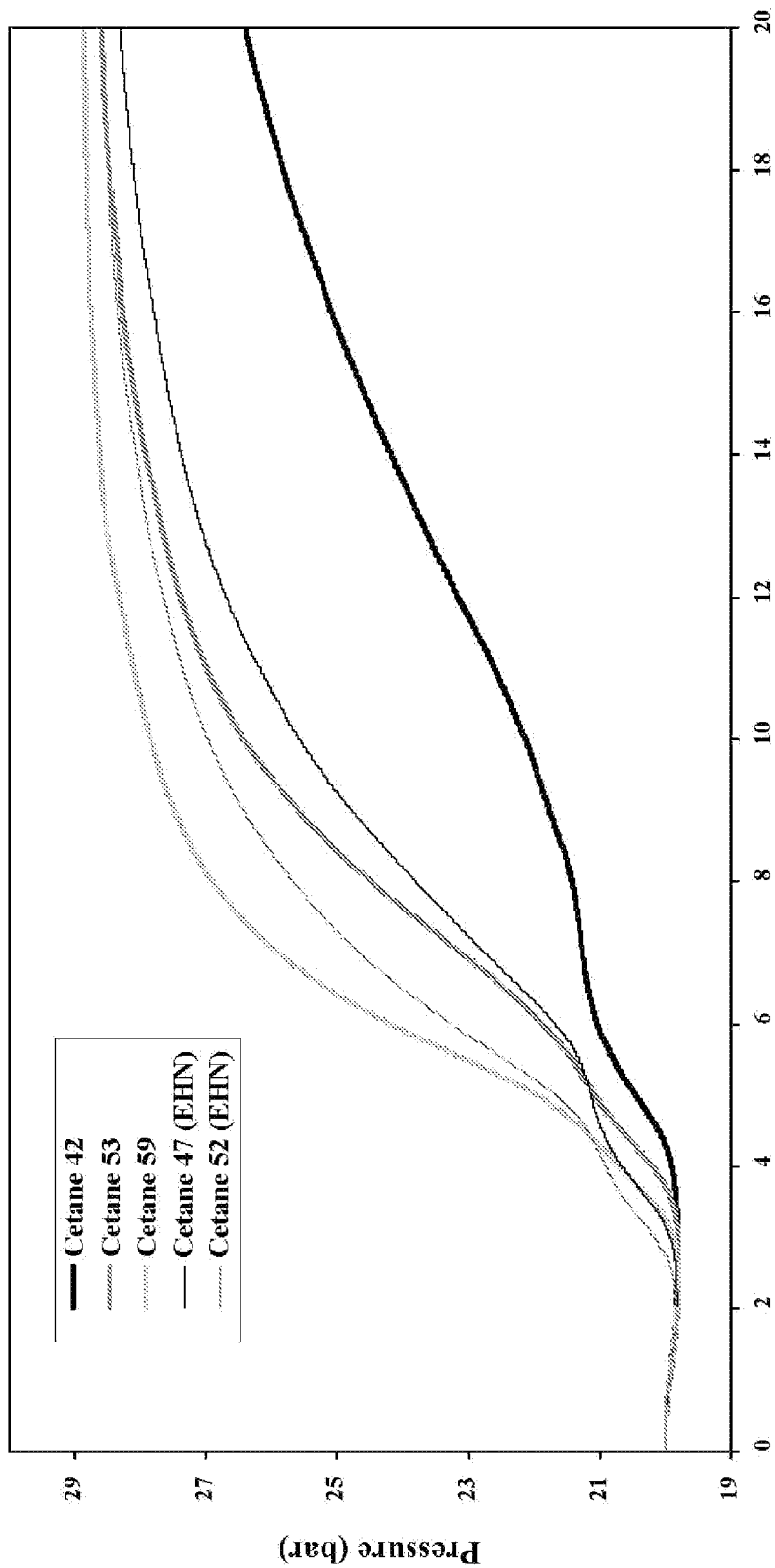
FIG. 9 depicts a plot of combustion samples using the apparatus of FIG. 1 showing two region profiles under conditions to optimize DCN calculations.
Figure 10:
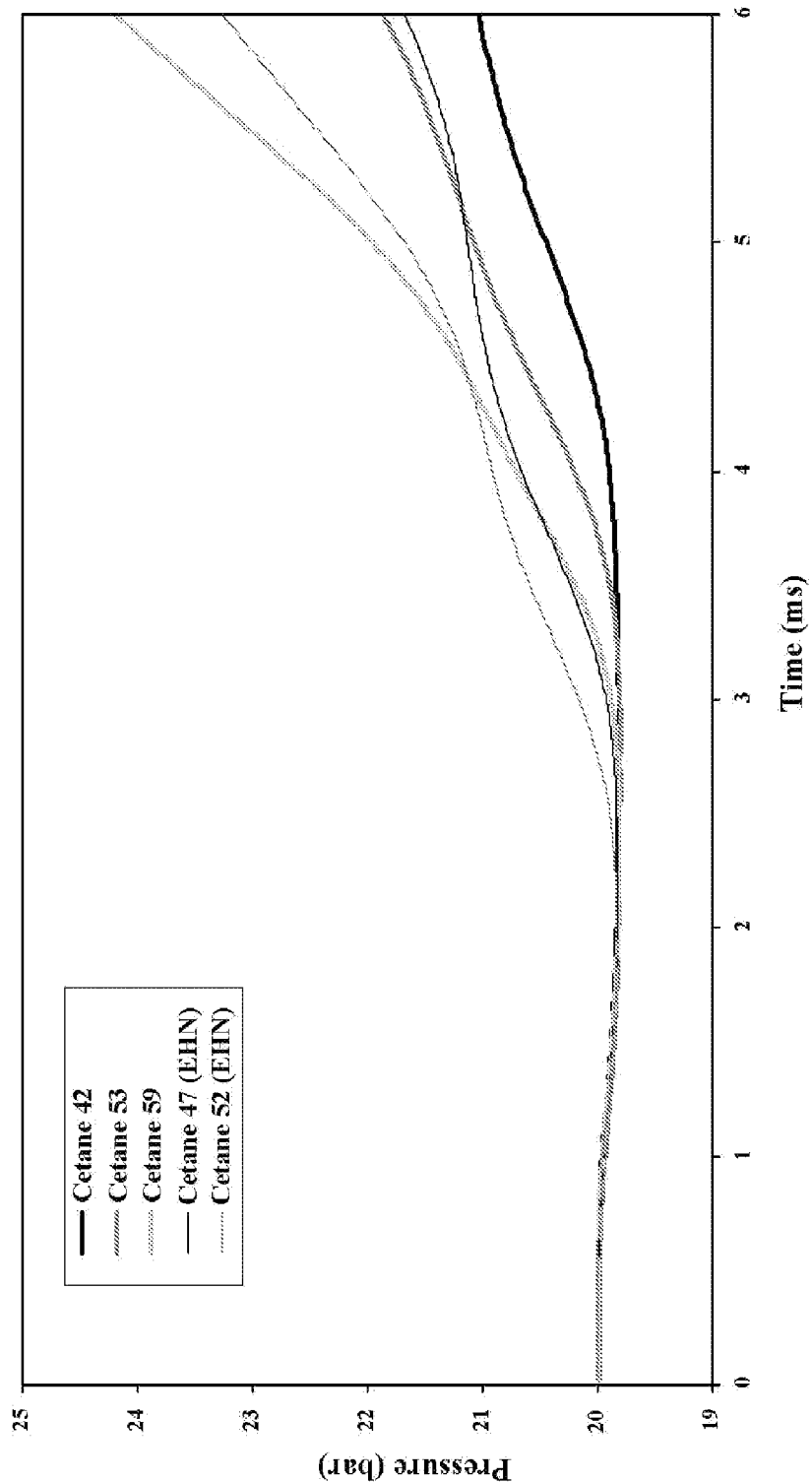
FIG. 10 depicts an expanded view of the data of FIG. 9.

Referring now to FIGS. 9&10, plots of combustion pressure/time profiles for two reference standards and three reference fluids/fuels are shown that were obtained using an apparatus of FIG. 1 at optimal time, temperature and pressure for use in selecting appropriate pressure/time data points from the A region and the B region of use in calculating DCN values of this invention using equations equation (I) through equation (VII).

The pressure waves or profiles using a modern injector CVCC apparatus typically are different from those obtained using conventional CVCC apparatuses in general use today, which generate profiles typically having only a combustion curve having a single profile or region, i.e., the curve is not capable of discriminating between early burning components and late burning components. The new CVCC apparatus such as the apparatus of FIG. 1 typically generates profiles having two combustion regions, the A region and the B region. It should be recognized that these regions may not represent separate or distinct curve segments, but one may appear as a shoulder on the other curve segment. Thus, the early burning components may appear as a shoulder on the curve of the late burning components. In certain embodiments, the present invention uses pressure/time data points from both the early ignition delay region and the later ignition delay region as independent variables in a series expansion equation about these points yielding improved derived cetane number values for middle distillate fluids and/or fuels as compared to the prior art method for calculating derived cetane number values. It should also be recognized that the two or more selected points can be selected so that one represents an early ignition delay and the other represents a late ignition delay so that the power series expansion equation (I) through equation (VII) will have appropriate independent variables for computing DCN values.

In certain embodiments, low chamber temperatures are used to improve the differentiation between derived cetane number values for samples that would give essentially the DCN value using the conventional ASTM method. The obtained pressure curves or profiles are sensitive to a volume of the injected sample so care should be exercised in sample injection. Additionally, stable stoichiometry (size of sample injected) is important for stable pressure data. The present invention is based on the inventor's recognition that more than one pressure/time data point (sometimes referred to herein as an ID measurement) along the pressure curve is required to differentiate between hydrocarbon fuels, cetane-improved fuels and bio-diesels and to generate DCN values for unknown middle distillate fluids/fuels that more closing match their corresponding CN values. The inventor has found that equations using only a single point ID measurement do not give satisfactory DCN determination for all types of samples. The DCN values obtained from these equations show large and unpredictable DCN value variances relative to their corresponding CN values. The present invention based on at least two point ID measurements, one from each region of the profile, yields DCN values that are better predictors of the corresponding CN values, i.e., the DCN values are closer to the CN values.

Table I tabulates CN and DCN values based on a single data point selected from the pressure/time curves for the tabulated samples.

TABLE I

Single ID Using Standard Linear Fit Method

| Sample | CN | ID | DCN | Delta |
|---|---|---|---|---|
| Low C Ref | 42.0 | 4.37 | | |
| High C Ref | 53.0 | 3.82 | | |
| Ultra High C Ref | 58.6 | 3.48 | | |
| NEG D-991 (contains EHN) | 51.2 | 2.98 | 69.0 | −17.8 |
| DP-3071 | 42.4 | 4.39 | 40.9 | 1.5 |
| DP-3072 | 42.1 | 4.52 | 38.3 | 3.8 |
| Ref 42 0.1 vol % EHN | 45.5 | 3.26 | 63.4 | −17.9 |
| Ref 42 0.5 vol % EHN | 52.0 | 2.86 | 71.4 | −19.4 |
| 42 can | 42.0 | 4.25 | 43.7 | −1.7 |
| PAC-1 (contains EHN) | | 3.41 | 60.4 | |
| Ref 42 B20 | 45.0 | 3.85 | 51.7 | −6.7 |
| Ref 58.6 B20 | 58.0 | 3.34 | 61.8 | −3.8 |
| B100 | 56.0 | 3.77 | 53.3 | 2.7 |

The data clearly demonstrate that the classical method for calculating DCN values yields DCN values having large variances or deviations from their corresponding CN values.

Table II tabulates CN and DCN values based on a single data point selected from the pressure/time curves for the tabulated samples in a power series expansion based on the single point, where the expansion is terminated at the second order.

TABLE II

Single ID Using Quadratic Fit Method Based on the Standard Fit Model

| Sample | CN | ID | ID$^2$ | DCN | Delta |
|---|---|---|---|---|---|
| Low C Ref | 42.0 | 4.37 | 19.0969 | | |
| High C Ref | 53.0 | 3.82 | 14.5924 | | |
| Ultra-High C Ref | 58.6 | 3.48 | 12.1104 | | |
| Ref 42 0.1 vol % EHN | 45.0 | 3.26 | 10.6276 | | |
| Ref 42 0.5 vol % EHN | 52.0 | 2.86 | 8.1796 | | |
| NEG D-991 (contains EHN) | 51.2 | 2.98 | 8.8804 | 51.6 | −0.4 |
| DP-3071 | 42.4 | 4.39 | 19.2721 | 36.7 | 5.7 |
| DP-3072 | 42.1 | 4.52 | 20.4304 | 32.3 | 9.8 |
| QA0081 | 55.4 | 3.65 | 13.3225 | 52.0 | 3.4 |
| QA0081 | 55.4 | 3.67 | 13.4689 | 51.8 | 3.6 |
| QA0081 | 55.4 | 3.65 | 13.3225 | 52.0 | 3.4 |
| 42 can | 42.0 | 4.25 | 18.0625 | 40.9 | 1.1 |
| 53 can | 53.0 | 3.74 | 13.9876 | 51.1 | 1.9 |
| PAC-1 (contains EHN) | | 3.41 | 11.6281 | 53.4 | |
| Ref 42 B20 | 45.0 | 3.85 | 14.8225 | 49.5 | −4.5 |
| Ref 58.6 B20 | 58.0 | 3.34 | 11.1556 | 53.5 | 4.5 |
| B100 | 56.0 | 3.77 | 14.2129 | 50.7 | 5.3 |

The table clearly demonstrates that including a second order term for calculating DCN values even in the standard fit model yields DCN values having smaller deviations or variances for most of the samples compared to actual CN values. Because this new calculation reduces the variance between the DCN values and the CN values, the present invention also includes the use of a second order term and/or higher order terms in the classical single ID linear fit method as set forth in ASTM standard method D 6890-03a.

Table III tabulates CN and DCN values based on a power series expansion based on the single point ID$_2$ from the B region of the pressure versus time profile using equation (I), where the expansion is terminated at the second order.

TABLE III

One Embodiment of A Method of This Invention

| Sample | CN | $ID_1$ | $ID_1^2$ | $ID_2$ | $ID_2^2$ | DCN | Delta |
|---|---|---|---|---|---|---|---|
| 42 | 42.0 | 4.37 | 19.0969 | 20 | 400 | | |
| 53 | 53.0 | 3.82 | 14.5924 | 8 | 64 | | |
| 58.6 | 58.6 | 3.48 | 12.1104 | 6.2 | 38.44 | | |
| Ref 42 0.1 vol % EHN | 45.0 | 3.26 | 10.6276 | 9.22 | 85.01 | | |
| Ref 42 0.5 vol % EHN | 52.0 | 2.86 | 8.1796 | 6.86 | 47.06 | | |
| NEG D-991 (contains EHN) | 51.2 | 2.98 | 8.8804 | 7.26 | 52.71 | 53.0 | −1.8 |
| DP-3071 | 42.4 | 4.39 | 19.2721 | 19.44 | 377.91 | 40.8 | 1.6 |
| DP-3072 | 42.1 | 4.52 | 20.4304 | 19.44 | 377.91 | 40.8 | 1.3 |
| QA0081 | 55.4 | 3.65 | 13.3225 | 6.98 | 48.72 | 54.2 | 1.2 |
| QA0081 | 55.4 | 3.67 | 13.4689 | 7.08 | 50.13 | 53.8 | 1.6 |
| QA0081 | 55.4 | 3.65 | 13.3225 | 6.98 | 48.72 | 54.2 | 1.2 |
| 42 can | 42.0 | 4.25 | 18.0625 | 17.58 | 309.06 | 37.9 | 4.1 |
| 53 can | 53.0 | 3.74 | 13.9876 | 7.46 | 55.65 | 52.3 | 0.7 |
| PAC-1 (contains EHN) | | 3.41 | 11.6281 | 6.72 | 45.16 | 55.3 | |
| Ref 42 B20 | 45.0 | 3.85 | 14.8225 | 9.92 | 98.41 | 44.1 | 0.9 |
| Ref 58.6 B20 | 58.0 | 3.34 | 11.1556 | 5.85 | 34.22 | 59.2 | −1.2 |
| B100 | 56.0 | 3.77 | 14.2129 | 7.16 | 51.27 | 53.5 | 2.5 |

The table clearly demonstrates that the DCN values derived from the present equations yield DCN values with even smaller deviations from their corresponding CN values.

Table IV tabulates CN and DCN values based a power series expansion based on the single point $ID_1$ from the A region of the pressure versus time profile using equation (I), where the expansion is terminated at the second order.

It should be recognized that the analyzing part of the system of this invention are designed to be coded into a software routine that will run on computer components of the analyzer of the CVCC. Thus, the components of the system and the steps of the method that required computations or calculations are designed to occur in software routines encoding the component or method step. Thus, equations (I-VII) are designed to be implemented on a computer, where the software in encoded so as to take a set of selected data points from a pressure versus time profile and calculate a derived cetane number value based on a software implementation of one or more of the equations (I-VII).

TABLE IV

Another Embodiment of A Method of This Invention

| Sample | CN | $ID_1$ | $ID_1^2$ | $ID_2$ | $ID_2^2$ | DCN | Delta |
|---|---|---|---|---|---|---|---|
| 42 | 42.0 | 4.37 | 19.0969 | 20 | 400 | | |
| 53 | 53.0 | 3.82 | 14.5924 | 8 | 64 | | |
| 58.6 | 58.6 | 3.48 | 12.1104 | 6.2 | 38.44 | | |
| Ref 42 0.1 vol % EHN | 45.0 | 3.26 | 10.6276 | 9.22 | 85.01 | | |
| Ref 42 0.5 vol % EHN | 52.0 | 2.86 | 8.1796 | 6.86 | 47.06 | | |
| NEG D-991 (contains EHN) | 51.2 | 2.98 | 8.8804 | 7.26 | 52.71 | 50.9 | 0.3 |
| DP-3071 | 42.4 | 4.39 | 19.2721 | 19.44 | 377.91 | 41.8 | 0.6 |
| DP-3072 | 42.1 | 4.52 | 20.4304 | 19.44 | 377.91 | 42.8 | −0.7 |
| QA0081 | 55.4 | 3.65 | 13.3225 | 6.98 | 48.72 | 56.1 | −0.7 |
| QA0081 | 55.4 | 3.67 | 13.4689 | 7.08 | 50.13 | 55.8 | −0.4 |
| QA0081 | 55.4 | 3.65 | 13.3225 | 6.98 | 48.72 | 56.1 | −0.7 |
| 42 can | 42.0 | 4.25 | 18.0625 | 17.58 | 309.06 | 39.2 | 2.8 |
| 53 can | 53.0 | 3.74 | 13.9876 | 7.46 | 55.65 | 54.7 | −1.7 |
| PAC-1 (contains EHN) | | 3.41 | 11.6281 | 6.72 | 45.16 | 55.7 | |
| Ref 42 B20 | 45.0 | 3.85 | 14.8225 | 9.92 | 98.41 | 46.5 | −1.5 |
| Ref 58.6 B20 | 58.0 | 3.34 | 11.1556 | 5.85 | 34.22 | 59.4 | −1.4 |
| B100 | 56.0 | 3.77 | 14.2129 | 7.16 | 51.27 | 56.1 | −0.1 |

The table clearly demonstrates that the DCN values derived from the present equations yield DCN values with even smaller deviations from their corresponding CN values.

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

I claim:

1. A method for calculating derived cetane number values using a constant volume combustion chamber apparatus capable of yielding a pressure versus time combustion profile, the method comprising the steps of:
    injecting a high pressure sample into the constant volume combustion chamber apparatus at a predetermined pressure and temperature;
    combusting the sample in the constant volume combustion chamber apparatus;
    measuring the pressure in the constant volume combustion chamber apparatus as a function of time after injection of the sample until combustion is complete;
    obtaining a pressure versus time combustion profile of the sample;
    selecting a plurality of data points from the pressure versus time combustion profile; and
    calculating a derived cetane number value from a power series expansion equation expanded about the selected plurality of data points and/or arithmetic combination of the selected plurality of data points using a set of expansion coefficients.

2. The method of claim 1, wherein the calculating step includes calculating an arithmetic ratio of the data points.

3. The method of claim 1, wherein the pressure versus time combustion profile has a plurality of combustion regions and the selecting step selects a single data point from each region.

4. The method of claim 1, wherein the pressure versus time combustion profile has a plurality of combustion regions and the selecting step selects a plurality of data points from each region.

5. The method of claim 1, wherein the power series expansion equation terminates with second order terms.

6. The method of claim 1, further comprising the steps of:
    prior to the injecting a high pressure sample step, injecting a high pressure calibration sample having a known cetane number value into the constant volume combustion chamber apparatus at a predetermined pressure and temperature;
    combusting the calibration sample in the constant volume combustion chamber apparatus to produce a calibration pressure versus time combustion profile;
    selecting a plurality of calibration data points from the calibration pressure versus time combustion profile; and
    computing a derived cetane number value from the power series expansion equation expanded about the selected plurality of calibration data points and/or ratios of the selected plurality of calibration data points.

7. The method of claim 1, wherein the power series expansion equation is selected from the group consisting of the form of equations (I, II and III):

$$DCN = C_{1a}*ID_1 + C_{2a}*ID_2 + C_{1b}*(ID_1)^2 + C_{2b}*(ID_2)^2 + I \qquad (I)$$

where DCN is the derived cetane number value, $ID_1$ is the data point selected from the first region, $ID_2$ is a data point selected from the second region, $C_{1a}$, $C_{1b}$, $C_{2a}$, and $C_{2b}$ are expansion coefficients and I is an intercept, $$DCN = C_{1a}ID_1 + C_{2a}ID_2 + C_{1b}(ID_1)^2 + C_{2b}(ID_2)^2 + C_{ra}ID_1/ID_2 + C_{rb}(ID_1/ID_2)^2 + I \quad \text{(II)}$$

where DCN is the derived cetane number value, $ID_1$ is a data point selected from the first region, $ID_2$ is a data point selected from the second region, $C_{1a}$, $C_{1b}$, $C_{2a}$, $C_{2b}$, $C_{ra}$, and $C_{rb}$ are coefficients and I is the intercept, and $$DCN = C_{ra}ID_1/ID_2 + C_{rb}(ID_1/ID_2)^2 + I \quad \text{(III)}$$

where DCN is the derived cetane number value, $ID_1$ is a data point selected from the first region, $ID_2$ is a data point selected from the second region, $C_{ra}$ and $C_{rb}$ are coefficients and I is the intercept.

8. The method of claim 1, wherein the power series expansion equation is selected from the group consisting of the form of equations (IV and V):

$$DCN = \sum_{i=1,\,j=1}^{i=m,\,j=n} c_{ij}ID_i^j + \sum_{k=1,\,l=1}^{k=m,\,l=n} c'_{kl}ID_k'^l + I \quad \text{(IV)}$$

where DCN is the derived cetane number value, $ID_i$ are the data points selected from the first region, $ID'_k$ are the data points selected from the second region, $c_{ij}$ and $c'_{kl}$ are expansion coefficients and I is the intercept, i is an integer representing a number of data points selected from the first region, j is an integer representing the number of terms in the expansion for the selected data points in the first region, k is an integer representing the number of data points selected from the second region, and l is an integer representing the number of terms in the expansion for the selected data points in the second region, and $$DCN = \sum_{i=1,\,j=1}^{i=m,\,j=n} c_{ij}ID_i^j + \sum_{k=1,\,l=1}^{k=o,\,l=p} c_{kl}ID_k^l + \sum_{\substack{ii=1,\,jj=1,\\kk=1}}^{\substack{ii=n,\,jj=o,\\kk=m+p}} c_{iijjkk}\left(\frac{ID_{ii}}{ID_{jj}}\right)^{kk} + I \quad \text{(V)}$$

where DCN is the derived cetane number value, $ID_i$ are data points selected from the A region of the profile representing an ignition delay of components in the A region, $ID_k$ are data points selected from the B region of the profile representing an ignition delay of components in the B region, and $ID_{ii}/D_{jj}$ are ratios where $ID_{ii}$ are selected data points from the A region and $ID_{jj}$ are selected points from the B region, $c_{ij}$, $c_{kl}$ and $c_{iijjkk}$ are coefficients and I is the intercept, i is an integer representing a number of data points selected from the A region, j is an integer representing the number of terms in the expansion for the selected data points in the A region, k is an integer representing the number of data points selected from the B region, l is an integer representing the number of terms in the expansion for the selected data points in the B region, ii is an integer representing the number of data points selected from the A region, jj is an integer representing the number of data points selected from the B region, kk is an integer representing the number of terms in the expansion for the ratios of selected data points from region A to selected data points from the B region.

9. The method of claim 1, wherein the power series expansion equation is selected from the group consisting of the form of equations (VI and VII):

$$DCN = \sum_{i=1}^{n} \sum_{j=1,\,k=1}^{j=m,\,k=o} c_{ijk}ID_j^k + I \quad \text{(VI)}$$

where DCN is the derived cetane number value, $ID_j$ are the data points selected from the $i^{th}$ region of the profile, where each region represents components having different ignition delay time and $c_{ijk}$ are expansion coefficients corresponding to the $i^{th}$ region, the $j^{th}$ point raised the $k^{th}$ power and I is the intercept, and $$DCN = \sum_{i=1}^{n} \sum_{j=1,\,k=1}^{j=m,\,k=o} c_{ijk}ID_j^k + \sum_{\substack{ii=1,\,jj=1,\\kk=1}}^{\substack{ii=m,\,jj=m,\\kk=o}} c_{iijjkk}\left(\frac{ID_{ii}}{ID_{jj}}\right)^{kk} + I \quad \text{(VII)}$$

where DCN is the derived cetane number value, $ID_j$ are data points selected from the $i^{th}$ region of the profile, where each region represents components having different ignition delay time and $c_{ijk}$ are expansion coefficients corresponding to the $i^{th}$ region, the $j^{th}$ point of the $i^{th}$ region raised the $k^{th}$ power, $ID_{ii}/D_{jj}$ are ratios of data points from different regions, $c_{iijjkk}$ are expansion coefficients corresponding to the $ii^{th}$ data point from one region and the $jj^{th}$ data point from a different region raised to the $kk^{th}$ power and I is the intercept.

10. The system of claim 1 wherein the calculating step is performed by a computer.

11. A method for calculating derived cetane number values using a constant volume combustion chamber apparatus capable of yielding a pressure versus time combustion profile, the method comprising the steps of:
  injecting a high pressure calibration sample having a known cetane number value into the constant volume combustion chamber apparatus at a predetermined pressure and temperature;
  combusting the calibration sample in the constant volume combustion chamber apparatus to produce a calibration pressure versus time combustion profile;
  selecting a plurality of calibration data points from the calibration pressure versus time combustion profile;
  calculating a derived cetane number value from a power series expansion equation expanded about the selected plurality of calibration data points and/or ratios of the selected plurality of calibration data points;
  injecting a high pressure sample into the constant volume combustion chamber apparatus at a predetermined pressure and temperature;
  combusting the sample in the constant volume combustion chamber apparatus;
  measuring the pressure in the constant volume combustion chamber apparatus as a function of time after injection of the sample until combustion is complete;
  obtaining a pressure versus time combustion profile of the sample;
  selecting a plurality of sample data points from the sample pressure versus time combustion profile; and
  calculating a derived cetane number value from a power series expansion equation expanded about the selected plurality of sample data points and/or ratios of the selected plurality of sample data points.

12. The method of claim 11, wherein each profile has a plurality of combustion regions and the two selecting steps select a single data point from each region.

13. The method of claim 11, wherein each profile has a plurality of combustion regions and the two selecting steps select a plurality of data points from each region.

14. The method of claim 11, wherein the power series expansion equation terminates with second order terms.

15. The method of claim 11, wherein the power series expansion equation is selected from the group consisting of the form of equations (I, II and III):

$$DCN = C_{1a}*ID_1 + C_{2a}*ID_2 + C_{1b}*(ID_1)^2 + C_{2b}*(ID_2)^2 + I \quad (I)$$

where DCN is the derived cetane number value, $ID_1$ is the data point selected from the first region, $ID_2$ is a data point selected from the second region, $C_{1a}$, $C_{1b}$, $C_{2a}$, and $C_{2b}$ are expansion coefficients and I is an intercept, $$DCN = C_{1a}ID_1 + C_{2a}ID_2 + C_{1b}(ID_1)^2 + C_{2b}(ID_2)^2 + C_{ra}ID_1/ID_2 + C_{rb}(ID_1/ID_2)^2 + I \quad (II)$$

where DCN is the derived cetane number value, $ID_1$ is a data point selected from the first region, $ID_2$ is a data point selected from the second region, $C_{1a}$, $C_{1b}$, $C_{2a}$, $C_{2b}$, $C_{ra}$ and $C_{rb}$ are coefficients and I is the intercept, and $$DCN = C_{ra}ID_1/ID_2 + C_{rb}(ID_1/ID_2)^2 + I \quad (III)$$

where DCN is the derived cetane number value, $ID_1$ is a data point selected from the first region, $ID_2$ is a data point selected from the second region, $C_{ra}$ and $C_{rb}$ are coefficients and I is the intercept.

16. The method of claim 11, wherein the power series expansion equation is selected from the group consisting of the form of equations (IV and V):

$$DCN = \sum_{i=1, j=1}^{i=m, j=n} c_{ij} ID_i^j + \sum_{k=1, l=1}^{k=m, l=n} c'_{kl} ID_k'^l + I \quad (IV)$$

where DCN is the derived cetane number value, $ID_i$ are the data points selected from the first region, $ID'_k$ are the data points selected from the second region, $c_{ij}$ and $ck_l$ are expansion coefficients and I is the intercept, i is an integer representing a number of data points selected from the first region, j is an integer representing the number of terms in the expansion for the selected data points in the first region, k is an integer representing the number of data points selected from the second region, and l is an integer representing the number of terms in the expansion for the selected data points in the second region, and $$DCN = \sum_{i=1, j=1}^{i=m, j=n} c_{ij} ID_i^j + \sum_{k=1, l=1}^{k=o, l=p} c_{kl} ID_k^l + \sum_{\substack{ii=1, jj=1, \\ kk=1}}^{\substack{ii=n, jj=o, \\ kk=m+p}} c_{iijjkk}\left(\frac{ID_{ii}}{ID_{jj}}\right)^{kk} + I \quad (V)$$

where DCN is the derived cetane number value, $ID_i$ are data points selected from the A region of the profile representing an ignition delay of components in the A region, $ID_k$ are data points selected from the B region of the profile representing an ignition delay of components in the B region, and $ID_{ii}/D_{jj}$ are ratios where $ID_{ii}$ are selected data points from the A region and $ID_{jj}$ are selected points from the B region, $c_{ij}$, $c_{kl}$ and $c_{iijjkk}$ are coefficients and I is the intercept, i is an integer representing a number of data points selected from the A region, j is an integer representing the number of terms in the expansion for the selected data points in the A region, k is an integer representing the number of data points selected from the B region, l is an integer representing the number of terms in the expansion for the selected data points in the B region, ii is an integer representing the number of data points selected from the A region, jj is an integer representing the number of data points selected from the B region, kk is an integer representing the number of terms in the expansion for the ratios of selected data points from region A to selected data points from the B region.

17. The method of claim 11, wherein the power series expansion equation is selected from the group consisting of the form of equations (VI and VII):

$$DCN = \sum_{i=1}^{n} \sum_{j=1, k=1}^{j=m, k=o} c_{ijk} ID_j^k + I \quad (VI)$$

where DCN is the derived cetane number value, $ID_j$ are the data points selected from the $i^{th}$ region of the profile, where each region represents components having different ignition delay time and $c_{ijk}$ are expansion coefficients corresponding to the $i^{th}$ region, the $j^{th}$ point raised the $k^{th}$ power and I is the intercept, and $$DCN = \sum_{i=1}^{n} \sum_{j=1, k=1}^{j=m, k=o} c_{ijk} ID_j^k + \sum_{\substack{ii=1, jj=1, \\ kk=1}}^{\substack{ii=m, jj=m, \\ kk=o}} c_{iijjkk}\left(\frac{ID_{ii}}{ID_{jj}}\right)^{kk} + I \quad (VII)$$

where DCN is the derived cetane number value, $ID_j$ are data points selected from the $i^{th}$ region of the profile, where each region represents components having different ignition delay time and $c_{ijk}$ are expansion coefficients corresponding to the $i^{th}$ region, the $j^{th}$ point of the $i^{th}$ region raised the $k^{th}$ power, $ID_{ii}/D_{jj}$ are ratios of data points from different regions, $c_{iijjkk}$ are expansion coefficients corresponding to the $ii^{th}$ data point from one region and the $jj^{th}$ data point from a different region raised to the $kk^{th}$ power and I is the intercept.

18. The system of claim 11 wherein the two calculating steps are performed by a computer.

19. A method for calculating derived cetane number values using a constant volume combustion chamber apparatus capable of yielding a pressure versus time combustion profile, the method comprising the steps of:
    combusting a calibration sample having a known cetane number value in the constant volume combustion chamber apparatus to produce a calibration pressure versus time combustion profile where the pressure versus time calibration profile has a first region corresponding to sample components having earlier ignition temperatures and a second region corresponding to sample components having later ignition temperatures;
    selecting at least one data point from each region of the calibration pressure versus time combustion profile;

computing a derived cetane number value from a power series expansion equation expanded about the selected data points;

burning a middle distillate sample in a constant volume combustion chamber apparatus;

measuring and storing a pressure versus time combustion profile of the middle distillate sample, where the pressure versus time profile has a first region corresponding to sample components having earlier ignition temperatures and a second region corresponding to sample components having later ignition temperatures;

selecting at least one sample data point from each region of the sample pressure versus time combustion profile; and calculating a derived cetane number value from a power series expansion equation expanded about the selected sample data points.

20. The method of claim 19, wherein the power series expansion equation terminates with second order terms.

21. The method of claim 19, wherein the equation is of the form of equation (I):

$$DCN = C_{1a}*ID_1 + C_{2a}*ID_2 + C_{1b}*(ID_1)^2 + C_{2b}*(ID_2)^2 + I \quad (I)$$

where DCN is the derived cetane number value, $ID_1$ is the data point selected from the first region, $ID_2$ is a data point selected from the second region, $C_{1a}$, $C_{1b}$, $C_{2a}$, and $C_{2b}$ are expansion coefficients and I is an intercept.

22. The method of claim 19, wherein the equation is selected from the group consisting of the form of equations (I, II and III):

$$DCN = C_{1a}*ID_1 + C_{2a}*ID_2 + C_{1b}*(ID_1)^2 + C_{2b}*(ID_2)^2 + I \quad (I)$$

where DCN is the derived cetane number value, $ID_1$ is the data point selected from the first region, $ID_2$ is a data point selected from the second region, $C_{1a}$, $C_{1b}$, $C_{2a}$, and $C_{2b}$ are expansion coefficients and I is an intercept, $$DCN = C_{1a}ID_1 + C_{2a}ID_2 + C_{1b}(ID_1)^2 + C_{2b}(ID_2)^2 + C_{ra}ID_1/ID_2 + C_{rb}(ID_1/ID_2)^2 + I \quad (II)$$

where DCN is the derived cetane number value, $ID_1$ is a data point selected from the first region, $ID_2$ is a data point selected from the second region, $C_{1a}$, $C_{1b}$, $C_{2a}$, $C_{2b}$, $C_{ra}$, and $C_{rb}$ are coefficients and I is the intercept, and $$DCN = C_{ra}ID_1/ID_2 + C_{rb}(ID_1/ID_2)^2 + I \quad (III)$$

where DCN is the derived cetane number value, $ID_1$ is a data point selected from the first region, $ID_2$ is a data point selected from the second region, $C_{ra}$ and $C_{rb}$ are coefficients and I is the intercept.

23. The method of claim 19, wherein the equation is selected from the group consisting of the form of equations (IV and V):

$$DCN = \sum_{i=1, j=1}^{i=m, j=n} c_{ij} ID_i^j + \sum_{k=1, l=1}^{k=n, l=n} c'_{kl} ID_k'^l + I \quad (IV)$$

where DCN is the derived cetane number value, $ID_i$ are the data points selected from the first region, $ID'_k$ are the data points selected from the second region, $c_{ij}$ and $c'_{kl}$ are expansion coefficients and I is the intercept, i is an integer representing a number of data points selected from the first region, j is an integer representing the number of terms in the expansion for the selected data points in the first region, k is an integer representing the number of data points selected from the second region, and l is an integer representing the number of terms in the expansion for the selected data points in the second region, and $$DCN = \sum_{i=1, j=1}^{i=m, j=n} c_{ij} ID_i^j + \sum_{k=1, l=1}^{k=o, l=p} c_{kl} ID_k^l + \sum_{\substack{ii=1, jj=1, \\ kk=1}}^{\substack{ii=n, jj=o, \\ kk=m+p}} c_{iijjkk} \left(\frac{ID_{ii}}{ID_{jj}}\right)^{kk} + I \quad (V)$$

where DCN is the derived cetane number value, $ID_i$ are data points selected from the A region of the profile representing an ignition delay of components in the A region, $ID_k$ are data points selected from the B region of the profile representing an ignition delay of components in the B region, and $ID_{ii}/D_{jj}$ are ratios where $ID_{ii}$ are selected data points from the A region and $ID_{jj}$ are selected points from the B region, $c_{ij}$, $c_{kl}$ and $c_{iijjkk}$ are coefficients and I is the intercept, i is an integer representing a number of data points selected from the A region, j is an integer representing the number of terms in the expansion for the selected data points in the A region, k is an integer representing the number of data points selected from the B region, l is an integer representing the number of terms in the expansion for the selected data points in the B region, ii is an integer representing the number of data points selected from the A region, jj is an integer representing the number of data points selected from the B region, kk is an integer representing the number of terms in the expansion for the ratios of selected data points from region A to selected data points from the B region.

24. The method of claim 19, wherein the equation is selected from the group consisting of the form of equations (VI and VII):

$$DCN = \sum_{i=1}^{n} \sum_{j=1, k=1}^{j=m, k=o} c_{ijk} ID_j^k + I \quad (VI)$$

where DCN is the derived cetane number value, $ID_j$ are the data points selected from the $i^{th}$ region of the profile, where each region represents components having different ignition delay time and $c_{ijk}$ are expansion coefficients corresponding to the $i^{th}$ region, the $j^{th}$ point raised the $k^{th}$ power and I is the intercept, and $$DCN = \sum_{i=1}^{n} \sum_{j=1, k=1}^{j=m, k=o} c_{ijk} ID_j^k + \sum_{\substack{ii=1, jj=1, \\ kk=1}}^{\substack{ii=m, jj=m, \\ kk=o}} c_{iijjkk} \left(\frac{ID_{ii}}{ID_{jj}}\right)^{kk} + I \quad (VII)$$

where DCN is the derived cetane number value, $ID_j$ are data points selected from the $i^{th}$ region of the profile, where each region represents components having different ignition delay time and $c_{ijk}$ are expansion coefficients corresponding to the $i^{th}$ region, the $j^{th}$ point of the $i^{th}$ region raised the $k^{th}$ power, $ID_{ii}/D_{jj}$ are ratios of data points from different regions, $c_{iijjkk}$ are expansion coefficients corresponding to the $ii^{th}$ data point from one region and the $jj^{th}$ data point from a different region raised to the $kk^{th}$ power and I is the intercept.

25. The method of claim 19, wherein the two selecting steps select a plurality of data points from the first region of each profile.

26. The method of claim 19, wherein the two selecting steps select a plurality of data points from the second region of each profile.

27. The method of claim 19, wherein the two selecting steps select a plurality of data points from each region of each profile.

28. The system of claim 19 wherein the two calculating steps are performed by a computer.

29. A method for determining coefficients of a series expansion equation for calculating derived cetane number values using a constant volume combustion chamber apparatus capable of yielding a pressure versus time combustion profile, the method comprising the steps of:
adjusting the chamber temperature and/or injection time by injecting a specified calibration fluid into the constant volume combustion chamber at a specified injection pressure, the calibration fluid having known ignition delay values;
injecting a set of samples having a known cetane number values into the constant volume combustion chamber apparatus at the specified injection pressure;
combusting the samples in the constant volume combustion chamber apparatus under controlled conditions to obtain pressure versus time combustion data to produce the pressure versus time combustion profile;
selecting a plurality of data points from the pressure versus time combustion profile, such plurality of data points corresponding to ignition delays of the set of samples;
computing the coefficients of the series expansion equation about the selected plurality of data points using regression.

30. A system for calculating derived cetane number values comprising:
a constant volume combustion chamber subsystem adapted to combust a high pressure sample of a middle distillate fluid/fuel in a controlled manner to produce pressure versus time data of the combustion; and
an analyzing subsystem in communication with the constant volume combustion chamber subsystem, wherein the analyzing subsystem is adapted to accumulate data during combustion of the sample to produce a pressure versus time combustion profile, to select at least one point from the pressure versus time data combustion profile and to calculate a derived cetane number based on a power series expansion equation expanded about the selected at least one point, where the coefficients of the series expansion equation are determined by minimizing a difference between the derived cetane number value and a cetane number value of a calibration sample having a known cetane number value.

31. The system of claim 30 wherein the constant volume combustion chamber subsystem comprises:
a combustion chamber having a fixed volume;
a heater adapted to heat the combustion chamber to a predetermined temperature;
a source of compressed air adapted to adjust the pressure of the combustion chamber to a predetermined pressure; and
a high pressure injection system for injecting a fuel sample into the combustion chamber.

32. The system of claim 31 wherein the constant volume combustion chamber subsystem further comprises a coolant pump adapted to cool the combustion chamber.

33. The system of claim 32 wherein the high pressure injector system further comprises an injector and a sample container wherein a sample from the sample container is delivered to the injector at an elevated predetermined pressure for injection into the combustion chamber.

34. The system of claim 33 wherein the constant volume combustion chamber subsystem further comprises a controller operably connected to the injector, the source of compressed air, and the coolant pump to maintain controlled combustion conditions.

35. The system of claim 34 wherein the constant volume combustion chamber subsystem further comprises a power supply.

36. The system of claim 35 wherein the constant volume combustion chamber subsystem further comprises an exhaust port.

37. The system of claim 30 wherein the analyzing subsystem comprises:
a plurality of sensors adapted to receive data from the combustion chamber; and
a computer for computing a derived cetane number value from a power series expansion equation.

38. The system of claim 37 wherein the analyzing subsystem further comprises an output device connected to the computer for outputting data.

39. The system of claim 38 wherein the output device is a display.

40. The system of claim 38 wherein the output device is a graphing device.

41. The system of claim 38 wherein the output device is a printer.

* * * * *